US012102284B2

(12) United States Patent
Kasumi

(10) Patent No.: US 12,102,284 B2
(45) Date of Patent: Oct. 1, 2024

(54) ENDOSCOPE APPARATUS, METHOD OF CONTROLLING ENDOSCOPE APPARATUS AND NON-TRANSITORY COMPUTER READABLE RECORDING MEDIUM RECORDING PROGRAM FOR CONTROLLING ENDOSCOPE APPARATUS

(71) Applicant: OLYMPUS CORPORATION, Tokyo (JP)

(72) Inventor: Makoto Kasumi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 743 days.

(21) Appl. No.: 17/064,798

(22) Filed: Oct. 7, 2020

(65) Prior Publication Data
US 2021/0113059 A1    Apr. 22, 2021

Related U.S. Application Data

(63) Continuation of application No. PCT/JP2019/007616, filed on Feb. 27, 2019.

(30) Foreign Application Priority Data

Apr. 11, 2018 (JP) ................................. 2018-076365

(51) Int. Cl.
*A61B 1/00* (2006.01)
*A61B 1/06* (2006.01)

(52) U.S. Cl.
CPC ...... *A61B 1/00006* (2013.01); *A61B 1/00016* (2013.01); *A61B 1/00018* (2013.01);
(Continued)

(58) Field of Classification Search
CPC ............ A61B 1/00006; A61B 1/00009; A61B 1/00011; A61B 1/00016–00018;
(Continued)

(56) References Cited

U.S. PATENT DOCUMENTS

| | | | |
|---|---|---|---|
| 2003/0228553 A1 | 12/2003 | Mandelkern et al. | |
| 2007/0070194 A1* | 3/2007 | Abe ................... | A61B 1/00016 348/72 |
| 2009/0247824 A1 | 10/2009 | Kawasaki et al. | |
| 2014/0184765 A1* | 7/2014 | King ..................... | A61B 1/042 348/65 |

(Continued)

FOREIGN PATENT DOCUMENTS

| | | |
|---|---|---|
| EP | 2106143 A1 | 9/2009 |
| EP | 3062514 A1 | 8/2016 |

(Continued)

OTHER PUBLICATIONS

International Search Report dated May 28, 2019 issued in PCT/JP2019/007616.

*Primary Examiner* — Ryan N Henderson
*Assistant Examiner* — Pamela F Wu
(74) *Attorney, Agent, or Firm* — Scully, Scott, Murphy & Presser, P.C.

(57) ABSTRACT

An endoscope apparatus, includes: a memory configured to hold setting information about operations respectively of a first endoscope and a second endoscope; and a processor. The processor is configured to: when detecting switching of the endoscope to be used between the first endoscope and the second endoscope, read the setting information for the endoscope after the switching, and use the setting information for setting for operation of the endoscope after the switching; and when the setting for operation of the endoscope in use is changed, update the setting information for the endoscope in use, and based on the updated setting information for the endoscope in use, update the setting information for the endoscope not in use, and record, in the memory, the updated setting information.

20 Claims, 10 Drawing Sheets

(52) U.S. Cl.
CPC ........ *A61B 1/00027* (2013.01); *A61B 1/0655* (2022.02); *A61B 2560/0475* (2013.01); *A61B 2560/0487* (2013.01)

(58) Field of Classification Search
CPC  A61B 1/00029; A61B 1/00032–00034; A61B 1/00108; A61B 1/0002–00022; A61B 1/00059; A61B 1/00062; A61B 1/00057; A61B 1/00112–00114; A61B 1/00147; A61B 1/00119; A61B 1/00121; A61B 1/00124; A61B 1/00126; A61B 1/0011; A61B 1/00105; A61B 1/00103; A61B 1/00066; A61B 1/00064; A61B 1/00055
USPC .......................................... 600/113, 118, 132
See application file for complete search history.

(56) References Cited

U.S. PATENT DOCUMENTS

| | | | |
|---|---|---|---|
| 2014/0267656 A1* | 9/2014 | Blanquart | A61B 1/00137 348/68 |
| 2015/0094537 A1* | 4/2015 | Kuramoto | A61B 1/0638 600/160 |
| 2016/0261846 A1 | 9/2016 | Kasumi et al. | |
| 2017/0332889 A1 | 11/2017 | Akiba et al. | |

FOREIGN PATENT DOCUMENTS

| | | |
|---|---|---|
| JP | 2007-061296 A | 3/2007 |
| JP | 2009-112644 A | 5/2009 |
| JP | 2009-233172 A | 10/2009 |
| WO | WO 2003/103528 A2 | 12/2003 |
| WO | WO 2015/083451 A1 | 6/2015 |
| WO | 2016/190120 A1 | 12/2016 |

* cited by examiner

ENDOSCOPE APPARATUS, METHOD OF CONTROLLING ENDOSCOPE APPARATUS AND NON-TRANSITORY COMPUTER READABLE RECORDING MEDIUM RECORDING PROGRAM FOR CONTROLLING ENDOSCOPE APPARATUS

CROSS REFERENCE TO RELATED APPLICATION

This application is a continuation application of PCT/JP2019/007616 filed on Feb. 27, 2019 and claims benefit of Japanese Application No. 2018-076365 filed in Japan on Apr. 11, 2018, the entire contents of which are incorporated herein by this reference.

BACKGROUND OF THE INVENTION

1. Field of the Invention

The present invention relates to an endoscope apparatus that can use a wired endoscope and a wireless endoscope, a method of controlling an endoscope apparatus, and a non-transitory computer-readable recording medium that records a control program for an endoscope apparatus.

2. Description of the Related Art

Conventionally, endoscopes that allow an elongated endoscope to be inserted into a body cavity or the like, and allow observation of a site to be examined and various treatments, have been widely used. Also in industrial fields, industrial endoscopes that allow observation and inspection of inner flaws, corrosion and the like, such as of boilers, turbines, engines and chemical plants, have been widely used.

An endoscope image obtained by an image pickup device of an endoscope is transmitted to a processor that performs signal processing. The processor applies signal processing to the image from the endoscope, and supplies the monitor with the image, which is to be displayed, and supplies a recording device with the image, which is to be recorded.

To transmit the endoscope image from the endoscope to the processor, an endoscope cable is used. By the endoscope cable, however, a movable range of the endoscope is restricted or operability of the endoscope is degraded in some cases. The endoscope cable may sometimes be entangled with another cable to cause a failure, such as disconnection. Accordingly, in recent years, a wireless endoscope that is mounted with a rechargeable battery, and wirelessly transmits an endoscope image to a processor or the like, has been developed.

Japanese Patent Application Laid-Open Publication No. 2009-112644 discloses an apparatus that allows a wired endoscope and a wireless endoscope to be connected to a processor. Through use of the apparatus in Japanese Patent Application Laid-Open Publication No. 2009-112644, for example, the wireless endoscope is normally used in consideration of usability, and when a battery of the wireless endoscope is exhausted, or in other cases, the endoscope is switched to the wired endoscope, which can continue observation. In other words, the wired endoscope can also be used as a backup for the wireless endoscope.

SUMMARY OF THE INVENTION

An endoscope apparatus according to one aspect of the present invention, includes: a memory configured to hold setting information about operations respectively of a first endoscope and a second endoscope, one of which is a wireless endoscope and another of which is a wired endoscope; and a processor. The processor is configured to: detect switching of an endoscope to be used between the first endoscope and the second endoscope; when detecting the switching of the endoscope to be used between the first endoscope and the second endoscope, read the setting information for the endoscope after the switching stored in the memory, and use the setting information for setting for operation of the endo scope after the switching; and when the setting for operation of the endoscope in use between the first and second endoscopes is changed, update the setting information for the endoscope in use stored in the memory, and based on the updated setting information for the endoscope in use, update the setting information for the endoscope not in use between the first and second endoscopes, and record, in the memory, the updated setting information as the setting information for the endoscope not in use.

A method of controlling an endoscope apparatus according to one aspect of the present invention, includes: detecting switching of an endoscope to be used between a first endoscope and a second endoscope, one of which is a wireless endoscope and another of which is a wired endoscope; when detecting the switching of the endoscope to be used between the first endoscope and the second endoscope, reading setting information for the endoscope after the switching stored in a memory that holds setting information about operations respectively of the first endoscope and the second endoscope, and using the setting information for setting for operation of the endoscope after the switching; and when the setting for operation of the endoscope in use between the first and second endoscopes is changed, updating the setting information for the endoscope in use stored in the memory, and based on the updated setting information for the endoscope in use, updating the setting information for the endoscope not in use between the first and second endoscopes, and recording, in the memory, the updated setting information as the setting information for the endoscope not in use.

A non-transitory computer-readable recording medium recording a control program for an endoscope apparatus according to one aspect of the present invention records the control program that is for causing a computer to execute procedures of: detecting switching of an endoscope to be used between a first endoscope and a second endoscope, one of which is a wireless endoscope and another of which is a wired endoscope; when detecting the switching of the endoscope to be used between the first endoscope and the second endoscope, reading setting information for the endoscope after the switching stored in a memory that holds setting information about operations respectively of the first endoscope and the second endoscope, and using the setting information for setting for operation of the endoscope after the switching; and when the setting for operation of the endoscope in use between the first and second endoscopes is changed, updating the setting information for the endoscope in use stored in the memory, and based on the updated setting information for the endoscope in use, updating the setting information for the endoscope not in use between the first and second endoscopes, and recording, in the memory, the updated setting information as the setting information for the endoscope not in use.

DETAILED DESCRIPTION OF THE PREFERRED EMBODIMENT

Figure 1:
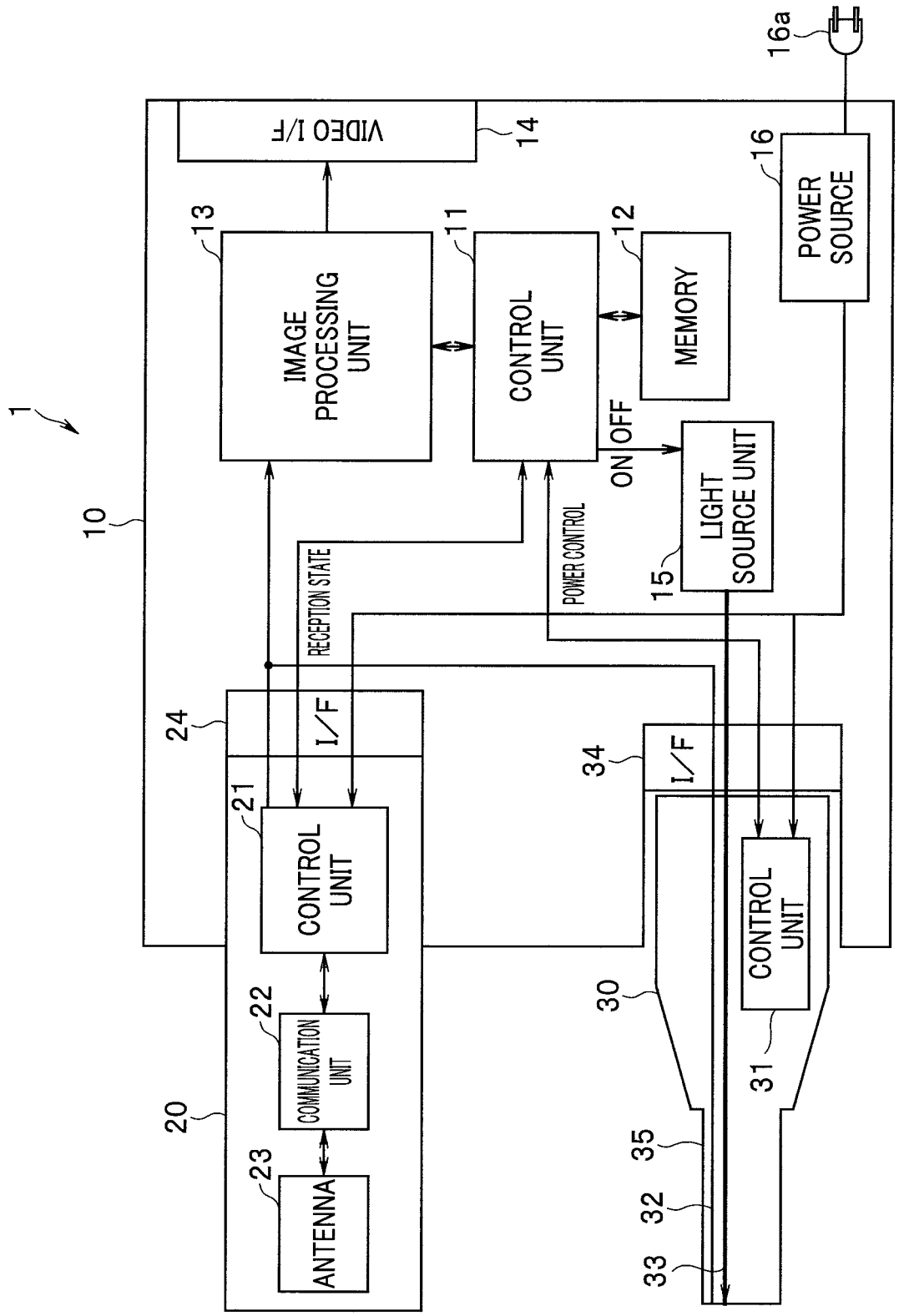
FIG. 1 is a block diagram showing a circuit configuration of a major part of an endoscope apparatus according to one embodiment of the present invention.

Hereinafter, referring to the drawings, an embodiment of the present invention will be described in detail.

Figure 2:
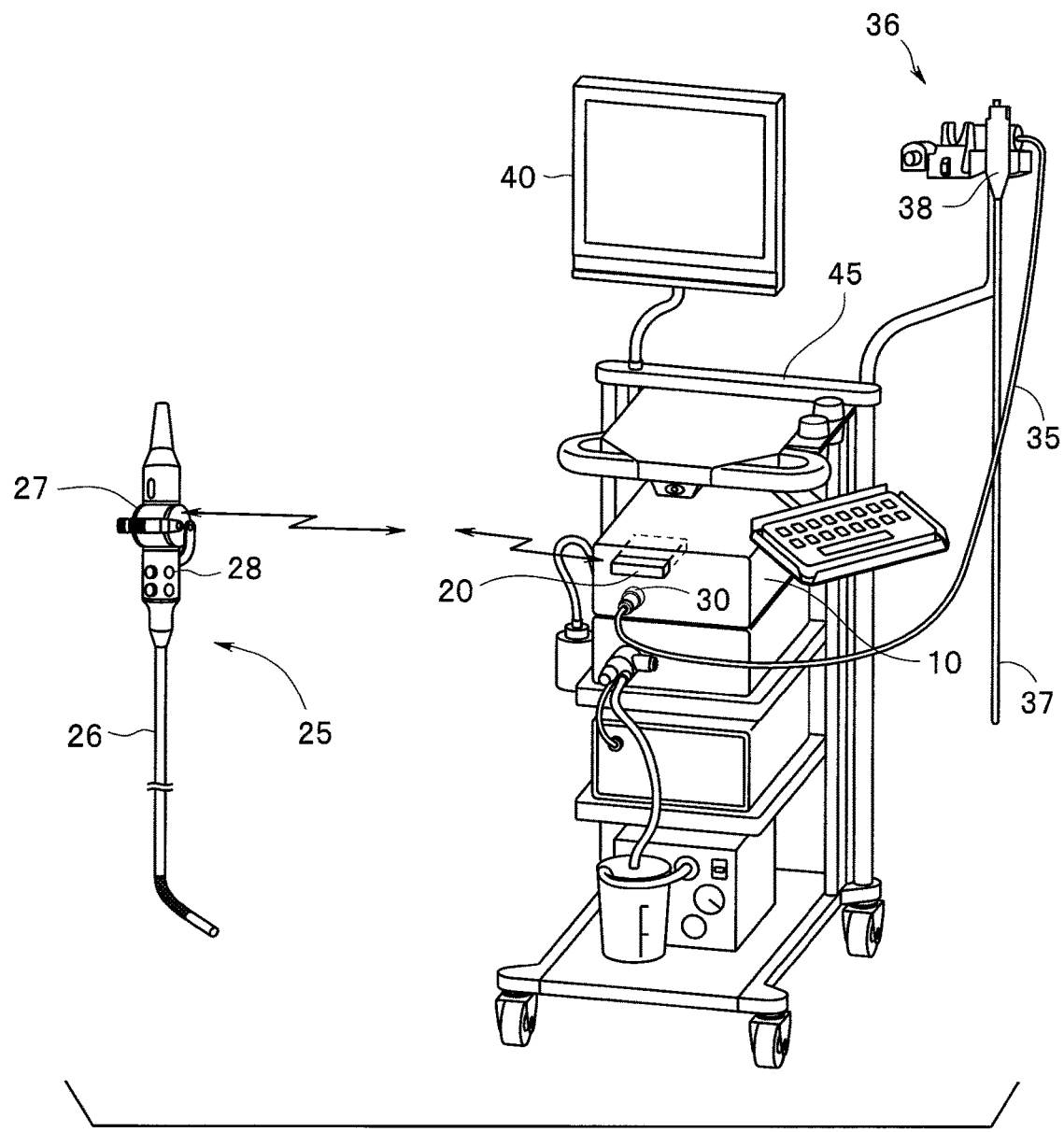
FIG. 2 is an explanatory diagram schematically showing an overall configuration of an endoscope system.
Figure 3:
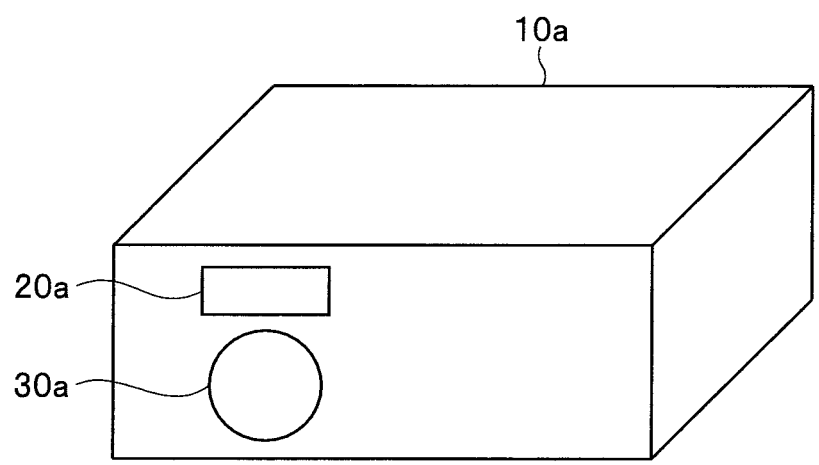
FIG. 3 is an explanatory diagram showing an appearance of a processor 10 in FIG. 1.

FIG. 1 is a block diagram showing a circuit configuration of a major part of an endoscope apparatus according to one embodiment of the present invention. FIG. 2 is an explanatory diagram schematically showing an overall configuration of an endoscope system. FIG. 3 is an explanatory diagram showing an appearance of a processor 10 in FIG. 1. The present embodiment stores setting information about an endoscope in use, and creates, in conformity with the setting information, setting information about an endoscope not in use and stores the created setting information. Accordingly, when the endoscope to be used is switched, smooth switching can be achieved to improve the usability.

First, referring to FIGS. 2 and 3, the endoscope system that adopts an endoscope apparatus 1 will be schematically described. The endoscope system in FIG. 2 includes a wireless endoscope 25, a wired endoscope 36, a processor 10, and a monitor 40. Various medical instruments, and the monitor 40 are arranged on a cart 45. The processor 10 to which a wireless unit 20 configuring a wireless device is attached is mounted on the cart 45. A housing 10a of the processor 10 is provided with an opening portion 20a and an opening portion 30a, and the wireless unit 20 is attached to the processor 10 at the opening portion 20a. A connector 30 connected to the wired endoscope 36 is attached to the opening portion 30a. Note that the medical instruments, for example, devices including an electrocautery device, an insufflation device and a video recorder, and a gas bottle filled with carbon dioxide are also mounted on the cart 45.

The wireless endoscope 25 is allowed to perform a photographing operation for typical endoscopic observation by being mounted with a battery, not shown, and has a wireless configuration of being connected wirelessly to the processor 10.

The wireless endoscope 25 includes an endoscope main body that includes an insertion portion 26 on a distal end side, and an operation portion 27 on a proximal end side. An image pickup unit that is not shown and includes an image pickup device including a CCD, a CMOS sensor or the like is arranged at a distal end portion of the insertion portion 26. The insertion portion 26 is provided with an illumination unit, not shown, for generating illumination light for illuminating an object. The illumination unit, which serves as a light source in the endoscope, is configured to illuminate the object with generated light as illumination light through a lens that is at the distal end of the insertion portion 26 and is not shown.

Return light from the object is incident through the lens, not shown, at the distal end of the insertion portion 26, and forms an image on an image pickup plane of the image pickup unit. The image pickup unit obtains an image-pickup image based on an object optical image through photoelectric conversion. The image pickup unit is configured to transmit the image-pickup image onto a board, not shown, in the operation portion 27, through a signal line, not shown, in the insertion portion 26. The board, not shown, provided for the operation portion 27 is mounted with various circuits that include an image processing circuit and a communication circuit performing signal transmission, which are not shown. An image pickup signal is wirelessly transmitted to the wireless unit 20 through the circuits.

A communication circuit embedded in the wireless endoscope 25 can transmit and receive, to and from the wireless unit 20, not only the image pickup signal, but also drive signals for driving the image pickup device and the illumination unit arranged in the insertion portion 26 and various setting information.

Note that the description has been made that the image pickup unit and the illumination unit are provided at the distal end of the insertion portion 26. Similar to a camera head, an image pickup unit may be provided for the operation portion 27. Alternatively, a light source may be provided for the operation portion 27 or the like to guide illumination light to the distal end of the insertion portion 26 through a light guide or the like.

The operation portion 27 is provided with a battery connection portion, not shown, for allowing a battery to be attached, and the battery is allowed to be detachably attached to the battery connection portion. Power from the battery is supplied to a power source unit mounted on the board in the operation portion 27 through a power source line, not shown, connected to the battery connection portion. The communication circuit embedded in the wireless endoscope 25 can also receive, from the wireless unit 20, a control signal for the power source unit. Power generation of the power source unit may be controlled by a control signal from the wireless unit 20.

As shown in FIG. 1, the wireless unit 20 includes an antenna 23, a communication unit 22, and a control unit 21. The communication unit 22 transmits and receives a wireless signal to and from the communication circuit of the wireless endoscope 25 via the antenna 23. The communication unit 22 provides the control unit 21 with a signal induced in the antenna 23, and transmits a signal from the control unit 21 to the communication circuit of the wireless endoscope 25 via the antenna 23.

The control unit 21 may include a processor using a CPU and the like, operate according to a program stored in a memory, not shown, and control each unit, or may achieve some or all of the functions by hardware electronic circuits. The control unit 21 controls the communication unit 22 to supply the wireless endoscope 25 with various control signals and drive signals and to receive an image pickup signal from the wireless endoscope 25. The control unit 21 outputs the received image pickup signal to an image processing unit 13 in the processor 10, via an I/F 24. The control unit 21 is configured to monitor a reception state of the communication unit 22, and to supply a reception state signal to a control unit 11 in the processor 10.

On the other hand, the wired endoscope 36 includes an elongated insertion portion 37 to be inserted into a body cavity. An operation portion 38 is provided at a rear end of the insertion portion 37. A universal cord 35 extends from the operation portion 38. An image pickup unit that is not shown and includes an image pickup device including a CCD, a CMOS sensor or the like is provided at a distal end portion of the insertion portion 37. An image pickup signal taken by the image pickup device is transmitted through the universal cord 35.

The connector 30 is provided at an extending end portion of the universal cord 35. As described above, the connector 30 is detachably connected to the processor 10 at the opening portion 30*a*. A light guide 33 that transmits illumination light is inserted into the connector 30, the universal cord 35, the operation portion 38 and the insertion portion 37. By connecting the connector 30 to the processor 10, illumination light generated at a light source unit 15 of the processor 10 is transmitted through the light guide 33, and is emitted through an illumination window, not shown, provided at the distal end portion of the insertion portion 37.

The distal end portion is provided with an observation window adjacent to the illumination window. An optical image of an illuminated subject is formed on an image pickup plane of the image pickup device through the observation window and an optical lens, not shown. The image pickup device obtains an image pickup signal based on an object optical image through photoelectric conversion. The image pickup signal is transmitted to the processor 10 through the signal line 32 in the insertion portion 37, the operation portion 38 and the universal cord 35.

The connector 30 is provided with a control unit 31. The control unit 31 may include an FPGA (field programmable gate array), or may include a processor that adopts a CPU and the like, not shown, and can control each unit according to the program stored in the memory.

The control unit 31 is configured to perform drive control of various electric circuits in the wired endoscope 36. For example, the control unit 31 controls operation states of exposure and reading of the image pickup device provided at the distal end portion of the insertion portion 37. The wired endoscope 36 is provided with a power source circuit, not shown, and the control unit 31 can also control the power source circuit. For example, the control unit 31 can control the power source circuit to set the power source voltage to be generated.

The processor 10 includes the control unit 11. The control unit 11 may include an FPGA, or may include a processor using a CPU and the like, and operate according to a program stored in a memory 12 and control each unit, or may achieve some or all of the functions by hardware electronic circuits. The control unit 11 controls each unit of the processor 10.

The opening portions 20*a* and 30*a*, which are provided for the housing 10*a* of the processor 10, are provided with the I/F 24 configuring a first interface and with an I/F 34 configuring a second interface, respectively. The wireless unit 20 is attached to the opening portion 20*a*. Accordingly, the control unit 11 is allowed to transmit and receive information to and from the control unit 21 of the wireless unit 20 via the I/F 24. The connector 30 is attached to the opening portion 30*a*. Accordingly, the control unit 11 is allowed to transmit and receive information to and from the control unit 31 in the connector 30 via the I/F 34. An image pickup signal obtained by the wireless endoscope 25 is supplied from the control unit 21 through the I/F 24 to the image processing unit 13. An image pickup signal obtained by the wired endoscope 36 is supplied through the signal line 32 via the I/F 34 to the image processing unit 13.

The image processing unit 13 is controlled by the control unit 11 to apply predetermined image signal processing to the inputted image pickup signal, to generate a video signal, and to output the generated video signal to a video I/F 14. The video I/F 14 converts the inputted video signal into a signal in conformity with predetermined transmission standards, and outputs the converted signal. For example, the video I/F 14 performs signal conversion that enables an endoscope image based on the inputted video signal to be displayed on the monitor 40. Thus, at the monitor 40, the endoscope image obtained by the wireless endoscope 25 or the wired endoscope 36 can be observed.

A power source 16 provided for the processor 10 can supply power to each unit of the processor 10, and supply the power to the wired endoscope 36 that includes the wireless unit 20 and the control unit 31. Power supply by the power source 16 is controlled by the control unit 11.

The processor 10 is provided with the light source unit 15. The light source unit 15 is controlled by the control unit 11 to generate illumination light, and to emit the generated illumination light to the light guide 33 of the wired endoscope 36. The control unit 11 can perform on-and-off control, light modulation control, and light emission mode control of switching between white light and special light of the light source unit 15.

The memory 12 may store a program that defines the operation of the control unit 11. The memory 12 is configured to store, as processor setting values, various setting information that define the operations of the wireless endoscope 25 and the wired endoscope 36.

For example, the control unit 11 stores information on whether the wireless unit 20 and the connector 30 are connected to the processor 10 or not, information on whether the wireless unit 20, the control unit 21 and the wireless endoscope 25 are in operation or not, information on whether the control unit 31 and the wired endoscope 36 are in operation or not, and information on power supply from the power source 16 to each unit, as processor setting values, in the memory 12. For example, the control unit 11 also stores status information about an on-and-off state, light modulation, and light emission mode of the light source unit 15, and status information about an on-and-off state, light modulation, and a light emission mode of switching between white light and special light of the illumination unit embedded in the wireless endoscope 25, as processor setting values, in the memory 12.

The control unit 11 can store such information, as the processor setting values, in the memory 12, and read the processor setting values stored in the memory 12 and set the setting values in the respective units. As described above, the control unit 11 is configured to convert the processor setting values during use of the wireless endoscope 25 into processor setting values for the wired endoscope 36 and to store the converted values in the memory 12, and to convert the processor setting values during use of the wired endoscope 36 into processor setting values for the wireless endoscope 25 and to store the converted values in the memory 12.

Note that the control unit 11 can change various settings about the observation state on the basis of a user operation to an operation portion, not shown, of the processor 10. The control unit 11 can update processor setting values in the memory 12 on the basis of the user operation. The wireless endoscope 25 and the wired endoscope 36 include respective memories, not shown. The memories are configured to be supplied by the control unit 11 with information corresponding to the processor setting values stored in the memory 12 of the processor 10, and to store the information.

In the present embodiment, the control unit 11, which serves as a determination unit, determines which one of the wireless endoscope 25 and the wired endoscope 36 is used, on the basis of a connection state between the wireless unit 20 and the connector 30 and of a reception state of the wireless unit 20. For example, one of the wireless unit 20 and the connector 30 is assumed to be connected to the processor 10. In such a case, the control unit 11 may determine that the wireless endoscope 25 is used if the wireless unit 20 is connected, and determine that the wired endoscope 36 is used if the connector 30 is connected. The control unit 11 may determine the endoscope to be used, on the basis of the reception state of the wireless unit 20, irrespective of the connection state between the wireless unit 20 and the connector 30. For example, if the image pickup signal is not received by the wireless unit 20 for a predetermined period, or if the reception state of the wireless unit 20 is degraded (wireless connection causes a failure), for example, if the S/N falls below a predetermined threshold, or if for example, the error rate exceeds a predetermined threshold, the control unit 11 may determine that the wired endo scope 36 is used. If the connector 30 is connected during use of the wireless endoscope 25, the control unit 11 may determine that the use is switched to use of the wired endoscope 36. If the wireless unit 20 is connected during use of the wired endoscope 36, the control unit 11 may determine that the use is switched to use of the wireless endoscope 25.

In any case, the control unit 11 monitors the connection state between the wireless unit 20 and the connector 30 and the reception state of the wireless unit 20 to thereby automatically perform control of switching the endoscope to be used. The control unit 11 can achieve smooth switching by providing the switched endoscope with setting information corresponding to the setting information on the endoscope before switching, and can obtain, in a relatively short time period, an observation image having an image quality, brightness, an observation mode and the like that are equivalent before and after switching.

Figure 4:
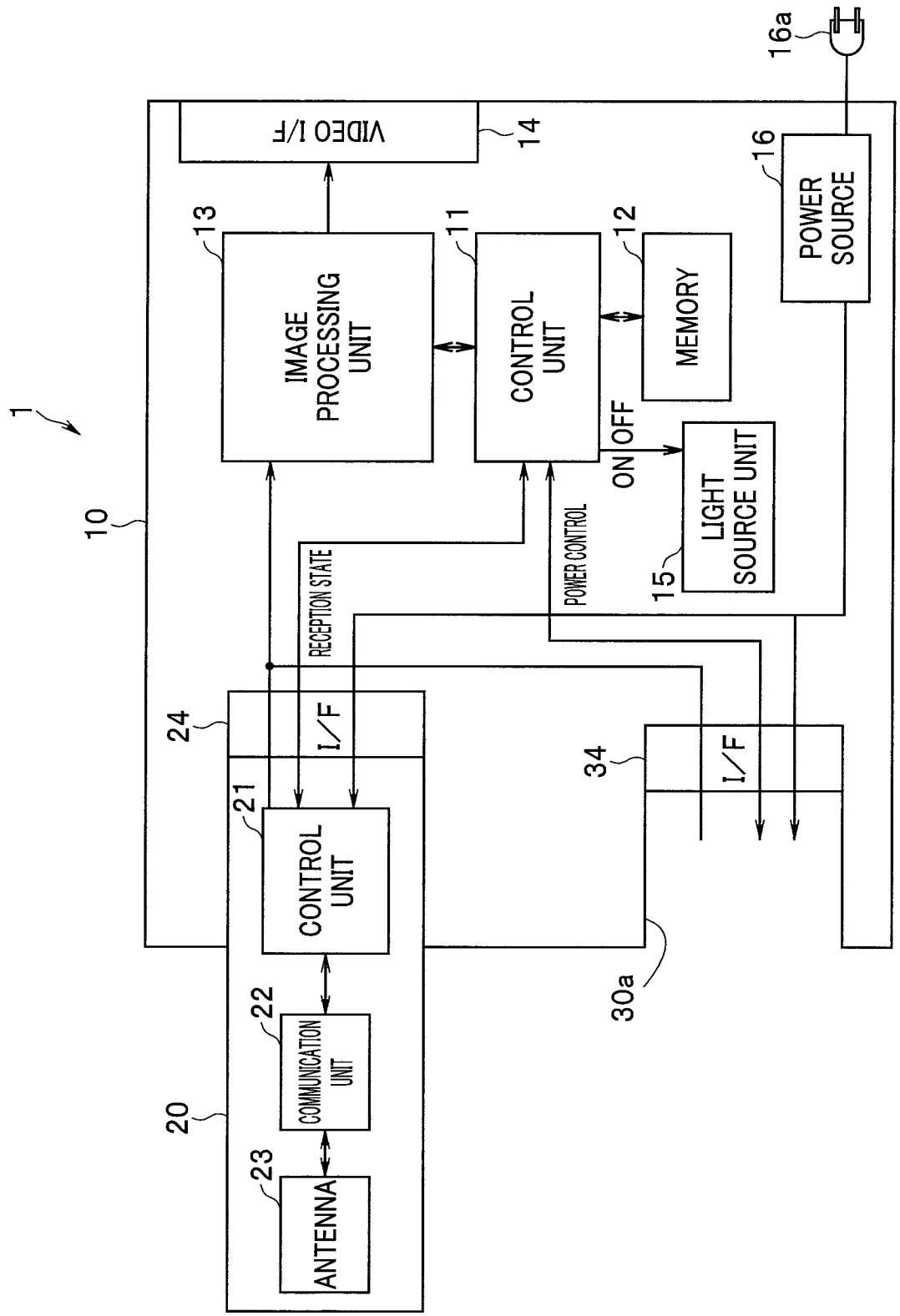
FIG. 4 is an explanatory diagram for illustrating an operation of the present embodiment.
Figure 5:
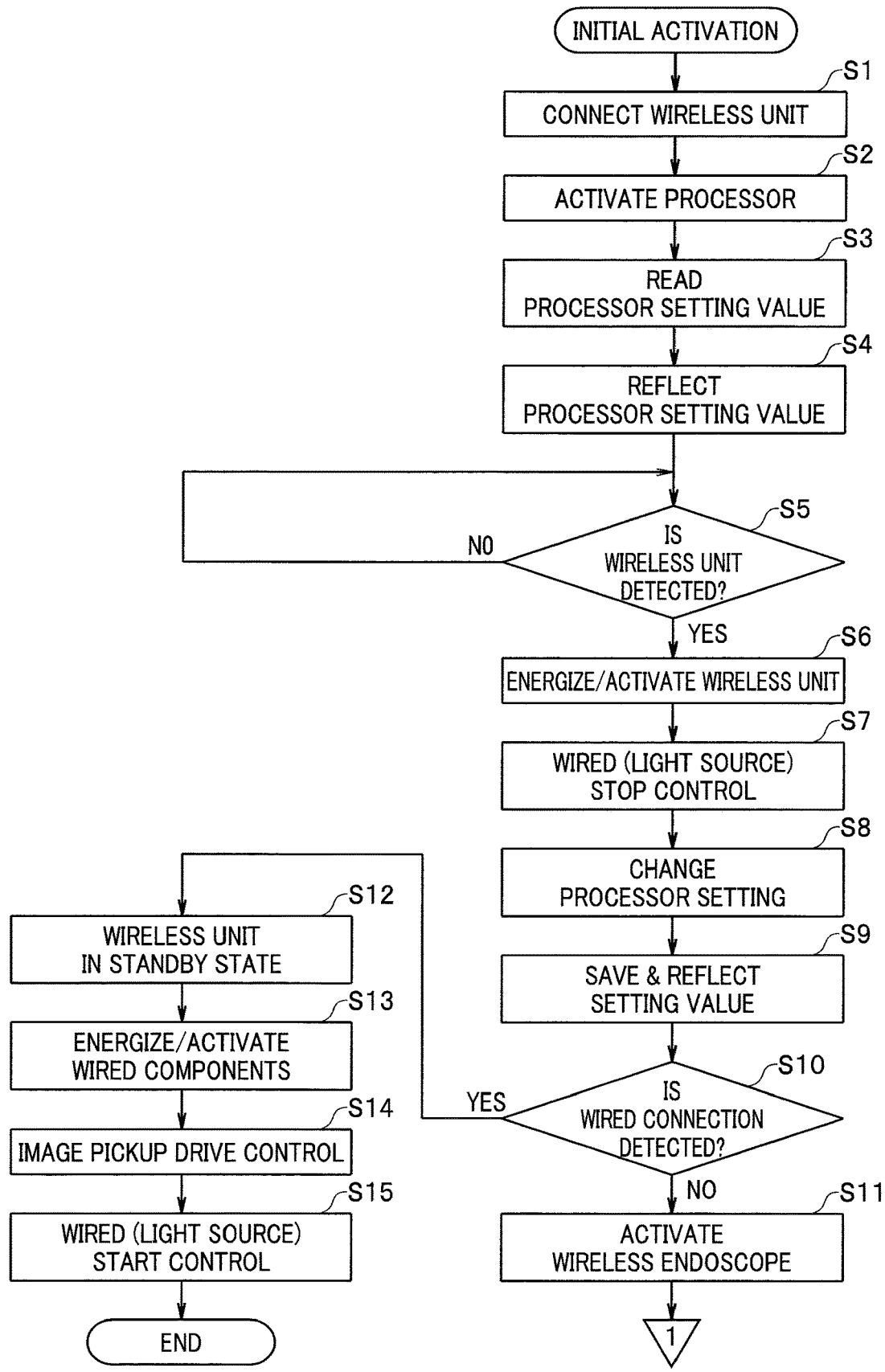
FIG. 5 is a flowchart for illustrating the operation of the present embodiment.
Figure 6:
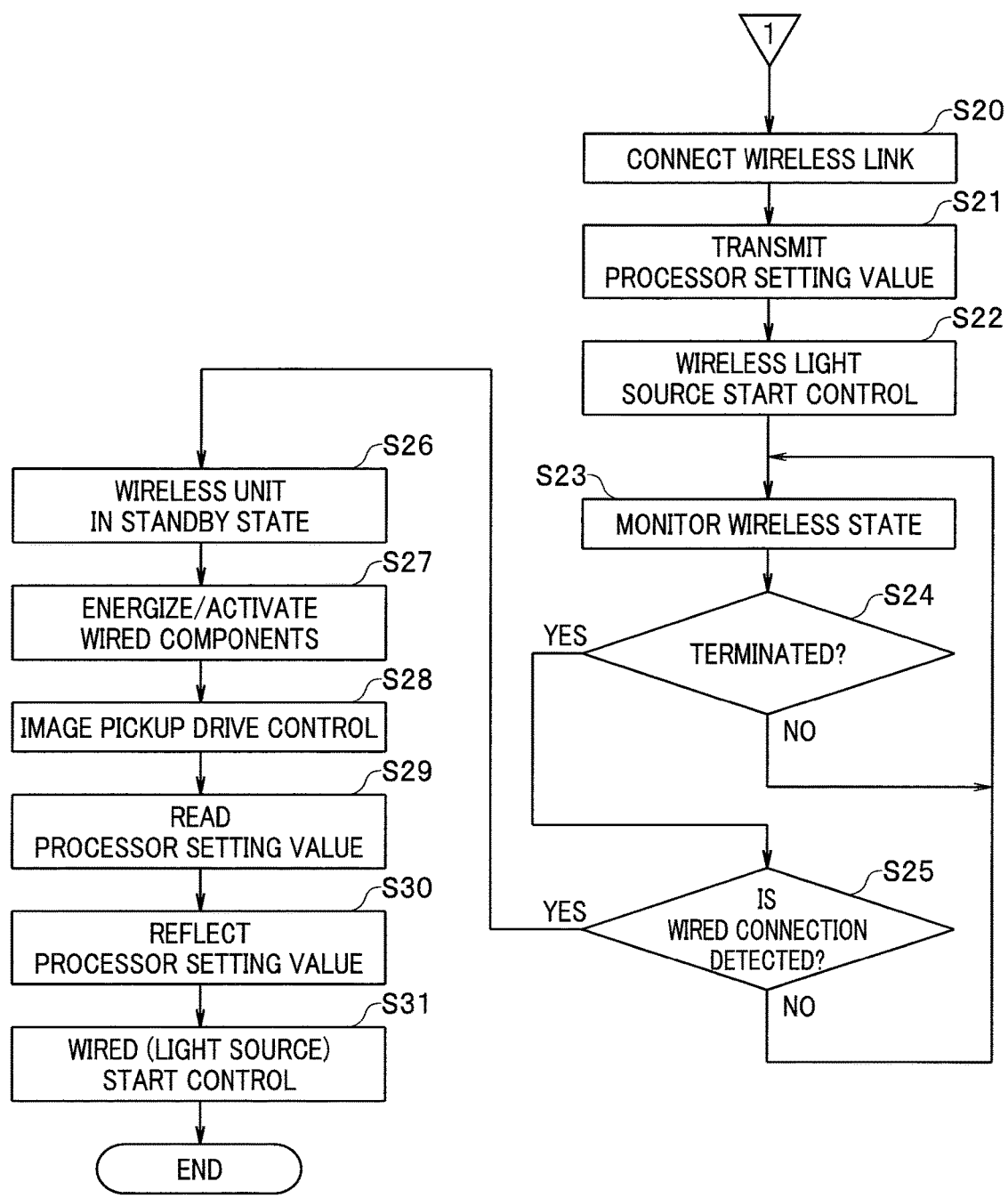
FIG. 6 is a flowchart for illustrating the operation of the present embodiment.
Figure 9:
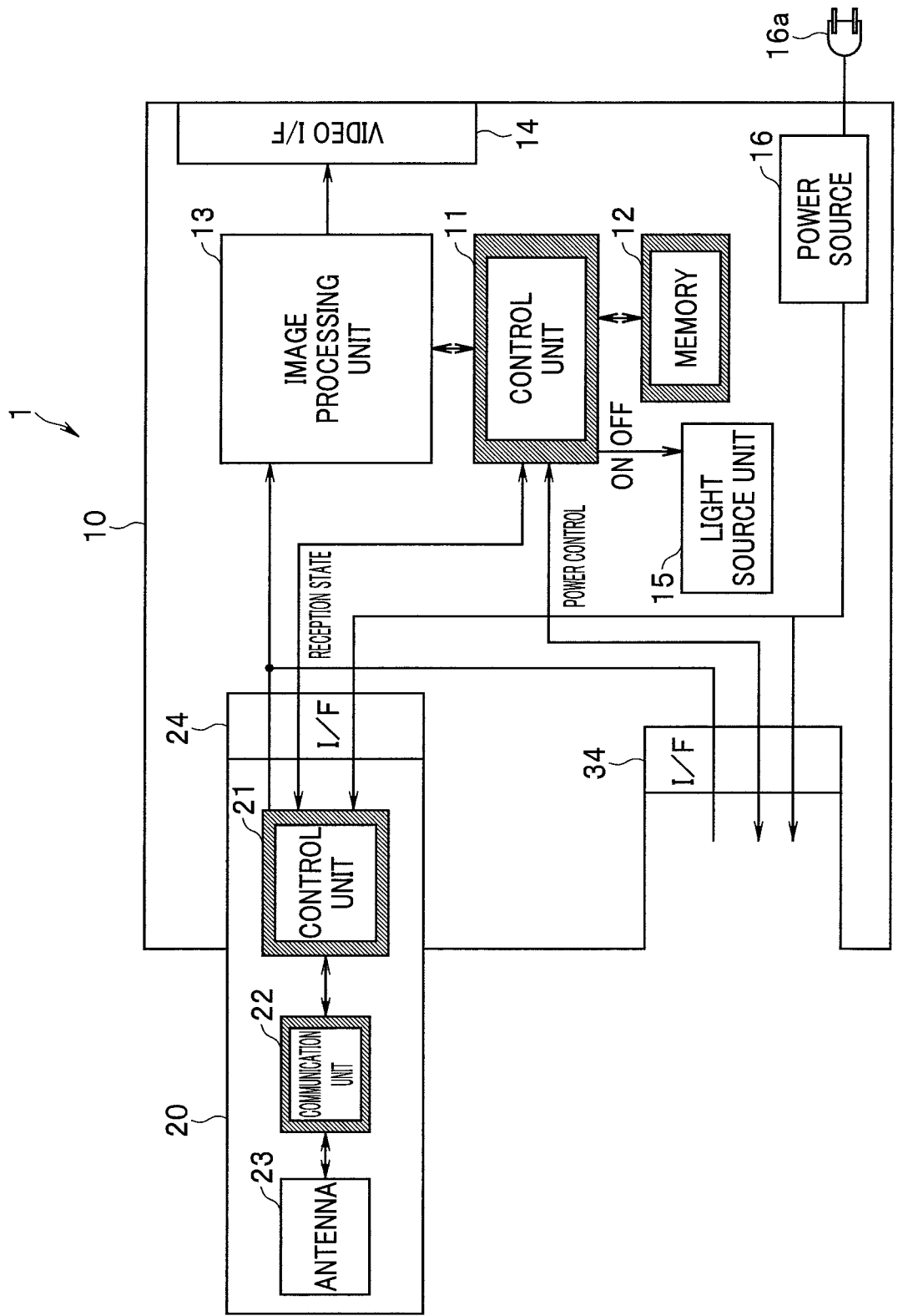
FIG. 9 is an explanatory diagram for illustrating the operation of the present embodiment.
Figure 10:
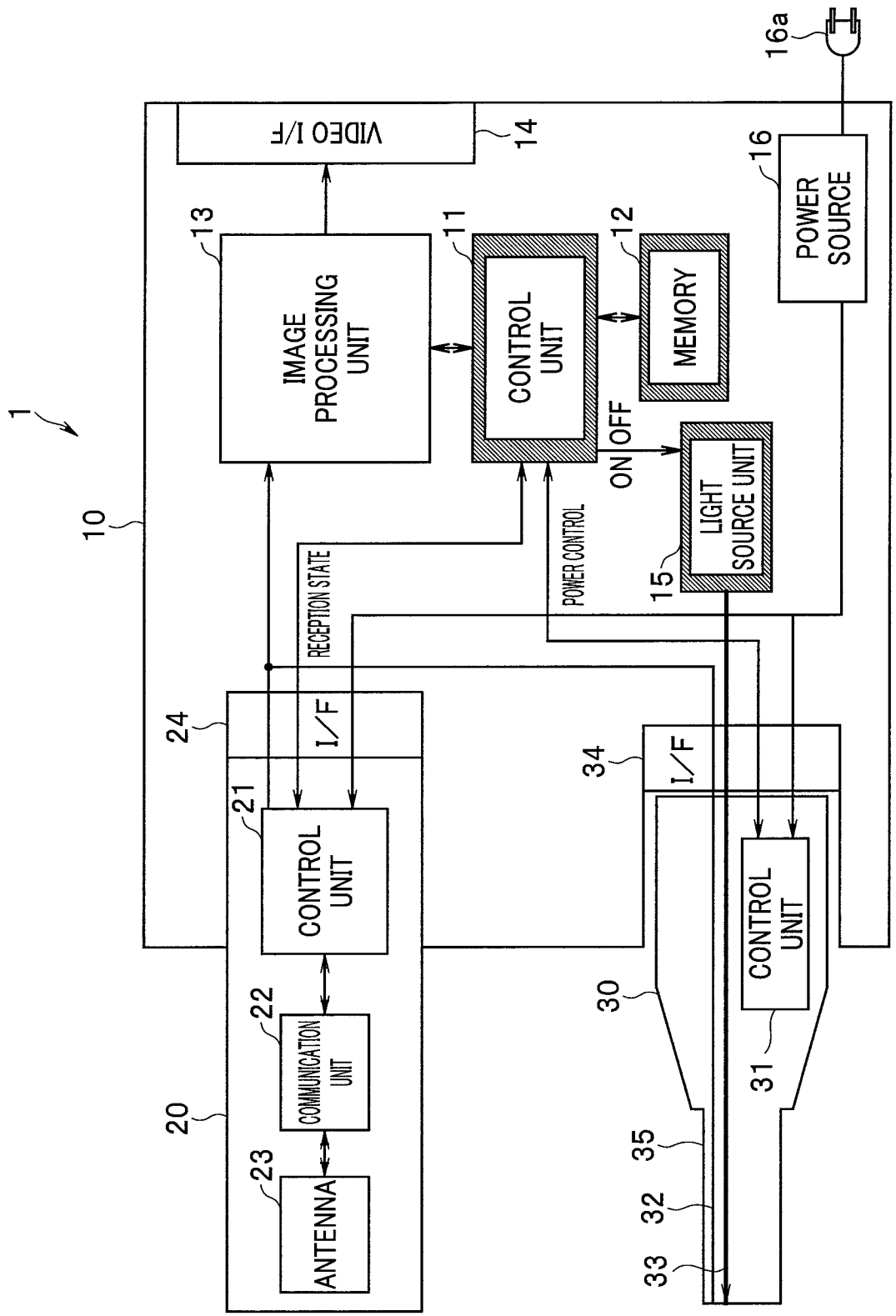
FIG. 10 is an explanatory diagram for illustrating the operation of the present embodiment.
Figure 11:
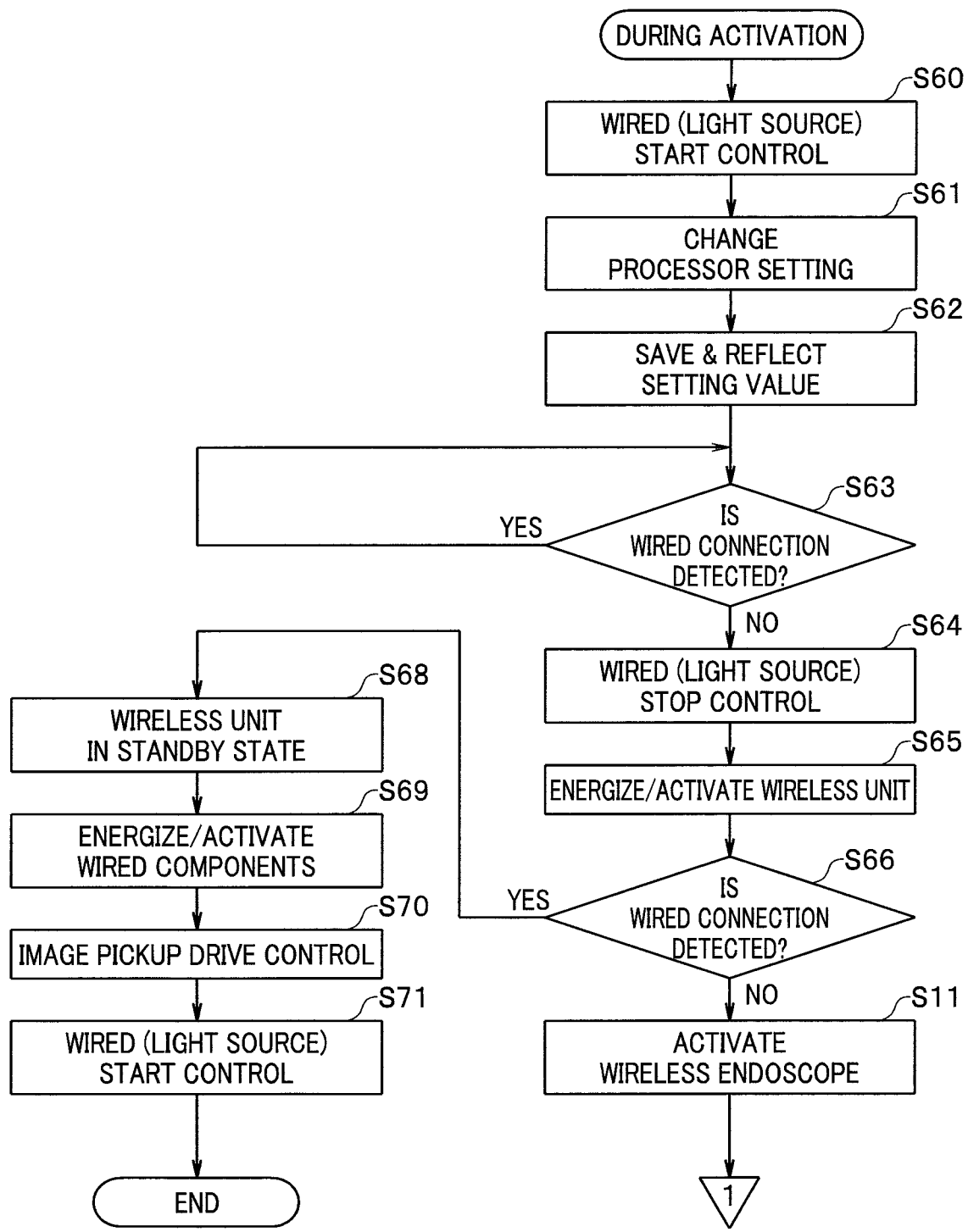
FIG. 11 is a flowchart for illustrating the operation of the present embodiment.

Next, the operation of the embodiment having such a configuration will be described with reference to FIGS. 4 to 11. FIGS. 4, 9 and 10 are explanatory diagrams for illustrating the operation of the present embodiment. FIGS. 5 to 8 and 11 are flowcharts for illustrating the operation of the present embodiment. Note that FIGS. 5 to 8 show the operation in the case of switching the wireless endoscope 25 in use to the wired endoscope 36. FIGS. 11 and 6 show the operation in the case of switching the wired endoscope 36 in use to the wireless endoscope 25. In FIGS. 5, 6 and 11, the same numeral encircled by a rectangle indicates coupling of processes.

(Switching by Wireless Endoscope from Initial Activation)

It is now assumed that at an initial activation, for endoscopic inspection, the wireless endoscope 25 is used but the wired endoscope 36 is not used. For example, a case where the connector 30 is not attached to the processor 10 is assumed. FIG. 4 shows the state, in which the connector 30 is not attached to the opening portion 30a of the housing 10a. On the other hand, the wireless unit 20 is attached to the opening portion 20a, and the wireless endoscope 25 is in a usable state.

Step S1 of FIG. 5 indicates that the wireless unit 20 is attached to the opening portion 20a, and electrical connection to the control unit 11 via the I/F 24 is enabled. When the processor 10 is activated in the state (step S2), the control unit 11 reads the processor setting values from the memory 12 in step S3. In step S4, the control unit 11 supplies the read processor setting values to the respective units. Accordingly, the respective units in the processor 10, the wireless unit 20, and the wireless endoscope 25 can perform respective operations according to the processor setting values.

Next, in step S5, the control unit 11 determines whether the wireless unit 20 is attached to the processor 10 or not. At the initial activation assumed in FIG. 5, the wireless endoscope 25 is used. In step S5, the control unit 11 is in a waiting state for attachment of the wireless unit 20 to the processor 10; the attachment is required to use the wireless endoscope 25.

When the control unit 11 detects that the wireless unit 20 is attached to the processor 10, the control unit 11 advances the processing to step S6, controls the power source 16 to start power supply to the wireless unit 20, supplies a control signal to the control unit 21, thus activating the wireless unit 20. Furthermore, in step S7, the control unit 11 turns off the light source unit 15 used for the wired endoscope 36 in use. Accordingly, the light source unit 15 is prevented from wastefully emitting illumination light.

In step S8, the control unit 11 accepts change of the processor setting values by the user. The user can change various settings about the observation state through the operation portion, not shown, of the processor 10. The control unit 11 updates the processor setting values stored in the memory 12 on the basis of the user operation for changing the settings (step S9). In such a case, the control unit 11 stores, in the memory 12, the processor setting values for the wireless endoscope 25 and the wired endoscope 36, in order to allow similar observation states to be achieved when the wireless endoscope 25 is used and when the wired endoscope 36 is used.

Note that when the processor setting values stored in the memory 12 are updated by the user operation or the like during use of one of the wireless endoscope 25 and the wired endoscope 36, the control unit 11 also updates the processor setting values stored in the memory 12 for the endoscope not in use, in conformity with the updated details.

In step S10, the control unit 11 detects wired connection. In other words, the control unit 11 determines whether the connector 30 is attached to the opening portion 30a of the housing 10a or not. In the case of the state in FIG. 4, the connector 30 is not attached to the processor 10, and the control unit 11 advances the processing to step S11. Note that in a case where the connector 30 is attached to the processor 10 at the time of connection determination in step S10, the control unit 11 advances the processing from step S10 to step S12.

In such a case, the control unit 11 brings the wireless unit 20 energized and activated in step S6 into the standby state (step S12). For example, in the standby state of the wireless unit 20, the control unit 21 continues the operation, and communication by the communication unit 22 is in the waiting state. Accordingly, power consumption required for wireless transmission can be suppressed.

In the next step S13, the control unit 11 controls the power source 16 to start energization to electronic components in the control unit 31 of the connector 30 and in the wired endoscope 36, and activates the electronic components. The control unit 31 then controls the image pickup unit to start picking up an image (step S14). In the next step S15, the control unit 11 turns on the light source unit 15 to generate illumination light. The illumination light is emitted from the distal end portion of the insertion portion 37 through the light guide 33 to the subject, and an image-pickup image of the subject is obtained.

Note that in steps S14 and S15, the processor setting values stored in the memory 12 are used. In other words, the processor setting values preliminarily stored in the memory 12 or the processor setting values updated in step S9 are used to control light modulation of the light source unit 15, exposure of the image pickup device and the like.

On the other hand, when the processor 10 is activated in the state in FIG. 4, the control unit 11 advances the processing from step S10 to step S11, and activates the wireless endoscope 25. In other words, in step S20 of FIG. 6, the wireless unit 20 is connected to the wireless link. The control unit 21 of the wireless unit 20 controls the communication unit 22 to establish wireless link to the wireless endoscope 25, and wirelessly transmit the processor setting values supplied from the control unit 11, through the antenna 23 to the wireless endoscope 25 (step S21).

Figure 7:
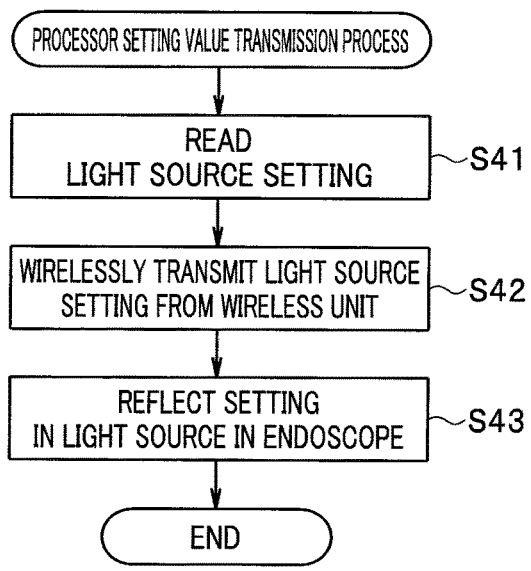
FIG. 7 is a flowchart for illustrating the operation of the present embodiment.

FIG. 7 shows a specific operation in step S21 of FIG. 6 about setting of the light source in the endoscope. In step S41 of FIG. 7, the control unit 11 reads, from the memory 12, the processor setting values about the light source setting. The information on the light source setting is transferred from the control unit 11 to the control unit 21, and the control unit 21 controls the communication unit 22 to wirelessly transmit the information on the light source setting (step S42). When the communication circuit in the wireless endoscope 25 receives the light source setting, the circuit sets the light source setting in the illumination unit serving as the light source in the endoscope (step S43).

The control unit 21 is controlled by the control unit 11 to start lighting of the illumination unit of the wireless endoscope 25 (step S22). As described above, the light modulation and the light emission mode of the illumination unit of the wireless endoscope 25 are controlled in conformity with the information on the light source setting (status information) stored in the memory 12.

Note that the wireless endoscope 25 sets the operation of each unit on the basis not only of the light source setting but also of the processor setting values received from the wireless unit 20. For example, the wireless endoscope 25 controls exposure and the like in conformity with the processor setting values, and drives the image pickup unit to pick up an image of the subject. An image pickup signal obtained by the wireless endoscope 25 is wirelessly transmitted and is received through the antenna 23 of the wireless unit 20. When the communication unit 22 receives the image pickup signal through the antenna 23, the control unit 21 supplies the received image pickup signal to the image processing unit 13 through the I/F 24. The image processing unit 13 generates a video signal by a predetermined image processing. The video signal is supplied to the monitor 40 through the video I/F 14, and an endoscope image obtained by the wireless endoscope 25 can be viewed on a display screen of the monitor 40.

The control unit 21 monitors the wireless state of the communication unit 22, and outputs information indicating the reception state to the control unit 11. The control unit 11 monitors the wireless state at the wireless unit 20 on the basis of the information indicating the reception state (step S23). In the present embodiment, during monitoring of the wireless state, the processor setting values that define the image quality, the brightness, the observation mode and the like of the observation image obtained by the wireless endoscope 25 are also monitored.

Figure 8:
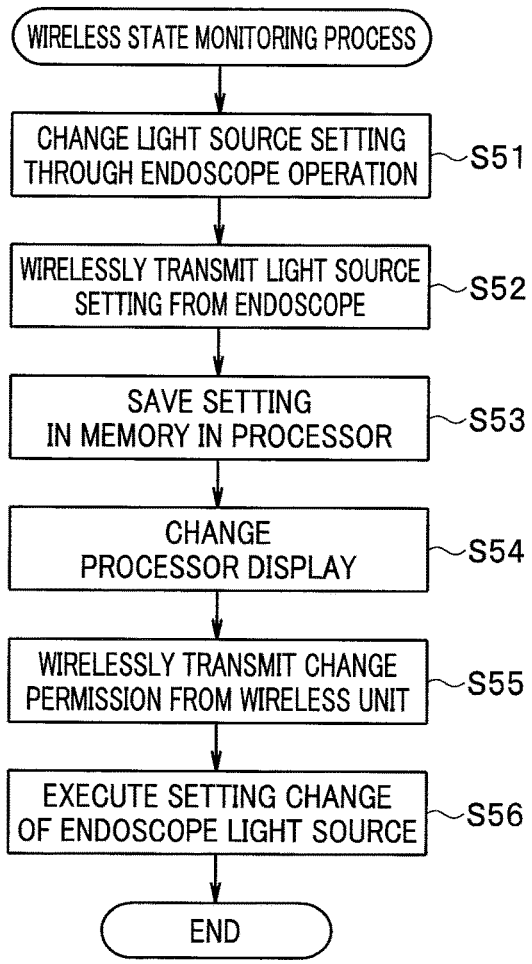
FIG. 8 is a flowchart for illustrating the operation of the present embodiment.

FIG. 8 shows a specific example of the monitoring process. It is now assumed that in the wireless endoscope 25, for example, the wireless endoscope 25 is operated to thereby change the setting of the illumination unit serving as the endoscope light source. For example, it is assumed that similar to a case where white light observation is switched to fluorescence observation, the light emission mode is switched from white light to special light. When an operation of changing the light emission mode is performed, the wireless endoscope 25 updates the light source setting stored in a memory, not shown, in conformity with the change (step S51). When the light source setting is changed, the wireless endoscope 25 wirelessly transmits the updated light source setting through a wireless circuit to the wireless unit 20 (step S52).

FIG. 9 shows a route along which the light source setting (status information) received by the wireless unit 20 is stored as the processor setting values through hatched blocks. When the control unit 21 of the wireless unit 20 receives the light source setting through the communication unit 22, the control unit 21 transfers the information to the control unit 11. The control unit 11 stores the transferred light source setting, as processor setting values, in a memory area for the wireless endoscope 25 in the memory 12.

Next, the control unit 11 updates display in conformity with the changed light source setting (step S54). For example, a display indicating a white light observation mode is changed to a display indicating a fluorescence observation mode. In step S55, the control unit 11 issues a notification about permission of changing the light source setting, and transfers the notification to the control unit 21. The control unit 21 of the wireless unit 20 controls the communication unit 22 to notify the wireless endoscope 25 of the permission of setting change (step S55). When the communication circuit of the wireless endoscope 25 receives the notification about permission of changing the setting, the illumination unit executes setting change of the endoscope light source (step S56). As described above, in the wireless endoscope 25, the setting change in response to the user operation is performed.

In the present embodiment, the control unit 11 stores the processor setting values in a recording area for the wireless endoscope 25 in step S53, converts the processor setting values stored in the memory area for the wireless endoscope 25 into values for the wired endoscope 36, and stores the converted processor setting values in the memory area for the wired endoscope 36 in the memory 12.

As a result of monitoring of the wireless state in step S23, the control unit 11 determines whether the wireless communication between the wireless endoscope 25 and the wireless unit 20 is terminated or not (step S24). If the wireless state is relatively favorable and the image-pickup image is continuously received, the control unit 11 determines that the wireless communication between the wireless endoscope 25 and the wireless unit 20 is not terminated. In such a case, the control unit 11 returns the processing to step S23, and continues to monitor the wireless state. In other words, until a NO determination is performed in step S24, observation images of the subject are normally obtained in the wireless endoscope 25.

It is now assumed that the control unit 11 determines termination of the wireless state in step S24 based on a certain reason. For example, in a case where the operation of the wireless unit 20 is stopped to replace batteries or the like, in a case where the operation of the wireless endoscope 25 is stopped, and in a case where a failure occurs in the wireless unit 20 or the wireless endoscope 25, the control unit 11 determines that termination of the wireless state occurs. In such cases, the control unit 11 advances the processing from step S24 to step S25, and detects presence or absence of wired connection.

In other words, the control unit 11 determines whether the connector 30 is attached to the opening portion 30a of the housing 10a or not. When the connector 30 is not attached to the processor 10, the control unit 11 returns the processing to step S23, and repeats detection of presence or absence of wireless state termination and wired connection. After the wireless state termination is resolved and wireless communication is recovered, the control unit 11 continues use of the wireless endoscope 25, and repeats detection of wireless state termination. If the wired connection is detected before the wireless state termination is resolved, the control unit 11 advances the processing from step S25 to step S26, and brings the wireless unit 20 into the standby state.

For example, in a case where the wireless endoscope 25 is stopped in order to replace batteries of the wireless endoscope 25, and the connector 30 is attached to the processor 10 in order to use the wired endoscope 36, the processing proceeds to step S26. Steps S26 to S28 are processes similar to steps S12 to S14. In step S27, the control unit 11 controls the power source 16 to start energization to electronic components in the control unit 31 of the connector 30 and in the wired endoscope 36, and activates the electronic components. The control unit 31 then controls the image pickup unit to start picking up an image (step S28).

In the present embodiment, in the next step S29, the control unit 11 reads the processor setting values from the memory 12, and sets the values in the respective units (step S30). As described above, each value of the processor setting values preliminarily stored in the memory 12 is mutually converted and stored so as to obtain similar observation states even in cases of using any of the wireless endoscope 25 and the wired endoscope 36. Furthermore, also as for the processor setting values updated by the user in step S9, each of the setting values for the wireless endoscope 25 and for the wired endoscope 36 is stored in the memory 12 by the control unit 11. The processor setting values changed by the user operation of the wireless endoscope 25 are also converted for the wired endoscope 36 and are stored.

In step S31, the control unit 11 turns on the light source unit 15 to generate illumination light. The illumination light is emitted from the distal end portion of the insertion portion 37 through the light guide 33 to the subject, and an image-pickup image of the subject is obtained. In such a case, the processor setting values stored in the memory 12 are used for the wired endoscope 36.

FIG. 10 shows a route along which the processor setting values read from the memory 12 by hatched blocks are set as the light source setting (status information) for the light source unit 15. The control unit 11 accesses the memory area for the wired endoscope 36 in the memory 12, and reads the processor setting values. The control unit 11 sets the read processor setting values, as the light source setting, in the light source unit 15. The processor values are used for light modulation control and mode control of the light source unit 15.

In any case among a case where the processor setting value is preliminarily stored in the memory 12, the case of being updated in step S9, and the case of being updated during monitoring in step S23, the values are mutually converted between use for the wireless endoscope 25 and use for the wired endoscope 36, and are stored in the memory areas for the wireless endoscope 25 and the wired endoscope 36 so as to obtain equivalent observation images irrespective of the endoscope to be used.

Consequently, illumination light equivalent to the light from the light source in the wireless endoscope 25 is emitted from the light source unit 15. In other words, in such a case, the light source unit 15 emits light in a special light mode in the fluorescence observation mode.

The processor setting values read from the memory 12 are also used for exposure control and the like of the image pickup device. The processor setting values correspond to the setting values used by the wireless endoscope 25 before endoscope switching. As for an observation image obtained from the wired endoscope 36 through light modulation control of the light source unit 15, exposure control of the image pickup device and the like, the image quality, brightness, observation mode and the like equivalent to the case of the observation image obtained from the wireless endoscope 25 are obtained. In other words, even when the endoscope in use is switched from the wireless endoscope 25 to the wired endoscope 36, the observation image equivalent to the observation image obtained by the wireless endoscope 25 can be obtained from the wired endoscope 36 in a relatively short time period.

(Switching During Activation of Wired Endoscope)

Next, referring to FIGS. 11 and 6, an example where the wired endoscope 36 in use is switched to the wireless endoscope 25 will be described.

It is now assumed that in step S15 of FIG. 5 or step S31 of FIG. 6 described above, the light source unit 15 is caused to emit light, and a state of obtaining the observation image of the subject using the wired endoscope 36 is achieved, in other words, during activation of the wired endoscope 36. Step S60 of FIG. 11 corresponds to the steps S15 and S31.

In step S61, the control unit 11 accepts change of the processor setting values by the user. The user can change various settings about the observation state through the operation portion, not shown, of the processor 10. The control unit 11 updates the processor setting values stored in the memory 12 on the basis of the user operation (step S62). In such a case, by the control unit 11, not only to update the processor setting values of the wired endoscope 36 in use but to obtain a similar observation state during use of the wireless endoscope 25, the processor setting values for the wired endoscope 36 are converted into processor setting values for the wireless endoscope 25 and subsequently stored in the memory area for the wireless endoscope 25 in the memory 12.

In the case of switching the endoscope in use from the wired endoscope 36 to the wireless endoscope 25, the user removes the connector 30 from the processor 10. In step S63, the control unit 11 detects wired connection. The control unit 11 determines whether the connector 30 is attached to the opening portion 30a of the housing 10a or not. Until the control unit 11 detects that the connector 30 is not attached to the processor 10, the control unit 11 repeats the process of step S63. Consequently, the wired endoscope 36 is used in a period during which the connector 30 is attached to the processor 10.

Note that referring to the example in FIG. 11, the description has been made that switching from the wired endoscope 36 to the wireless endoscope 25 is determined by removal of the connector 30 from the processor 10. Alternatively, even if the connector 30 is still attached to the processor 10, switching from the wired endoscope 36 to the wireless endoscope 25 may be determined by attachment of the wireless unit 20, having been removed from the processor 10, to the processor 10.

When the connector 30 is removed from the processor 10, the control unit 11 determines that an instruction of switching from the wired endoscope 36 to the wireless endoscope 25 is issued, advances the processing to step S64, stops light emission from the light source unit 15, supplies the power from the power source 16 to the wireless unit 20, and activates the wireless unit 20 (step S65). In the next step S66, the control unit 11 detects presence or absence of wired connection according to whether the connector 30 is attached to the processor 10 or not.

When the wired connection is temporarily terminated owing to a reason, such as of a contact failure of the connector 30, the control unit 11 determines, in step S66, that the wired connection is achieved. In such a case, the control unit 11 advances the processing from step S66 to step S68. Steps S68 to S71 are processes similar to steps S12 to S15. In step S68, the control unit 11 returns the wireless unit 20 to the standby state, subsequently controls the power source 16 to start energization to electronic components in the control unit 31 of the connector 30 and in the wired endoscope 36, and activates the electronic components (step S69). The control unit 31 then controls the image pickup unit to start image pickup in step S70, and restarts light emission from the light source unit 15 in step S71.

In step S66, if wired connection is not detected, the control unit 11 advances the processing to step S11. The step S11 is the same process as the process in step S11 of FIG. 5. In step S11, the control unit 11 activates the wireless endoscope 25. Subsequently, the individual steps in FIG. 6 are sequentially executed.

In other words, a wireless link is established, the processor setting values stored in the memory 12 are transferred to the wireless endoscope 25, and the wireless endoscope 25 obtains an observation image in conformity with the processor setting values. The processor setting values in such a case are setting values corresponding to various setting values for the wired endoscope 36 immediately before switching from the wired endoscope 36 to the wireless endoscope 25. The wireless endoscope 25 can obtain an observation image equivalent to the observation image obtained by the wired endoscope 36.

Note that in the above description, the example where the wireless unit 20 is brought into the standby state during use of the wired endoscope 36 has been described. Alternatively, the wireless unit 20 may be intermittently driven with a predetermined period, during use of the wired endoscope 36. In such a case, it can also be determined whether the wireless endoscope 25 becomes usable or not at the intermittent driving. For example, in a case where to replace batteries of the wireless endoscope 25, the endoscope to be used is switched from the wireless endoscope 25 to the wired endoscope 36, and the battery replacement of the wireless endoscope 25 is completed and image pickup is allowed, and subsequently the wireless unit 20 intermittently performs wireless communication and determines the wireless state is favorable, switching may be performed so as to automatically return the endoscope to be used from the wired endoscope 36 to the wireless endoscope 25.

In the above description, the example is described where the initial activation is with the wireless endoscope 25, and the endoscope to be used is switched from the wireless endoscope 25 to the wired endoscope 36 and is further switched from the wired endoscope 36 to the wireless endoscope 25. In an inverted manner, the technique is also similarly applicable in a similar manner to a case where the initial activation is with the wired endoscope 36, and the endoscope to be used is switched from the wired endoscope 36 to the wireless endoscope 25 and is further switched from the wireless endoscope 25 to the wired endoscope 36.

As described above, according to the present embodiment, in the case of use with both the endoscopes that are the wireless endoscope and the wired endoscope being switched, the setting values of both the endoscopes are stored, and the setting values of the endoscope not in use are converted into corresponding values in conformity with the setting values of the endoscope in use and are stored. At the time of switching of the endoscope to be used, observation images equivalent before and after switching can be obtained in a short time period. Switching of the endoscope to be used is automatically determined according to termination of communication with the wireless endoscope, and to whether the endoscope to be used is connected to the processor or not. Smooth switching of the endoscope to be used can be achieved without the user's complicated switching operation and parameter setting operation. And, at the time of switching, the observation image can be obtained in a relatively short time period. Accordingly, the usability can be improved. When the wireless endoscope is not used, the power supply to the wireless unit is suppressed, and wasteful power consumption can be reduced.

The present invention is not limited directly to each embodiment described above. In an implementation stage, the components may be modified and embodied in a range without departing from the gist. Various inventions can be formed by appropriate combination of a plurality of components disclosed in each embodiment described above. For example, some components among all the components indicated in the embodiment may be removed. Furthermore, components in different embodiments may be appropriately combined.

What is claimed is:

1. An endoscope apparatus comprising:
a memory configured to hold first setting information about an operation of a first endoscope in use and second setting information about an operation of a second endoscope not in use, one of the first endoscope and the second endoscope being a wireless endoscope and another of the first endoscope and the second endoscope being a wired endoscope; and
a processor configured to:
detect a switching signal for switching from the first endoscope in use to the second endoscope not in use;
when detecting the switching signal, read the second setting information stored in the memory, and use the second setting information for setting an observation function of the second endoscope after switching from the first endoscope to the second endoscope; and
when the setting for an observation function of the first endoscope in use is changed, update the first setting information for the first endoscope in use stored in the memory, and based on the updated first setting information for the first endoscope in use, update the second setting information for the second endoscope not in use, in the memory, and reflect the updated second setting information in the setting information for the second endoscope not in use.

2. The endoscope apparatus according to claim 1, further comprising:

a first interface configured to be connectable to a wireless device, the wireless device wirelessly transmitting and receiving information to and from the wireless endoscope; and a second interface configured to be connectable to a connector connected to the wired endoscope, wherein the processor is configured to detect the switching signal, based on a detection result of at least one of a first detection of detecting connection between the wireless device and the first interface or connection between the connector and the second interface, or a second detection of detecting wireless connection to the wireless device.

3. The endoscope apparatus according to claim 2,
wherein the first endoscope is the wireless endoscope, and the second endoscope is the wired endoscope.

4. The endoscope apparatus according to claim 3,
wherein the processor is configured to detect the switching signal based on the detection result of the second detection in case the wireless connection between the wireless device and the wireless endoscope is a failure.

5. The endoscope apparatus according to claim 3,
wherein when the detection result indicating that a wireless connection state of the wireless device is continued is obtained, the processor is configured to perform control of stopping activation of the second endoscope, and wherein when the detection result indicating that the wireless connection state of the wireless device is discontinued is obtained, the processor is configured to perform control of activation of the second endoscope.

6. The endoscope apparatus according to claim 1,
wherein the first endoscope is the wireless endoscope, and the second endoscope is the wired endoscope.

7. The endoscope apparatus according to claim 6, further comprising:

a first interface to which a wireless device is connectable, the wireless device wirelessly transmitting and receiving information to and from the wireless endoscope; and a second interface connectable to a connector connected to the wired endoscope, wherein when a detection result indicating switching of the endoscope to be used from the first endoscope to the second endoscope is obtained, the processor is configured to limit power supply to the wireless device.

8. The endoscope apparatus according to claim 6,
wherein in a case where the processor switches the endoscope to be used from the first endoscope to the second endoscope, the processor is configured to:

intermittently drive the wireless device with a predetermined period during use of the second endoscope to determine whether the first endoscope becomes usable or not; and when the first endoscope is determined to be usable during use of the second endoscope, perform switching of the endoscope to be used from the second endoscope to the first endoscope.

9. The endoscope apparatus according to claim 1,
wherein the setting information for the wireless endoscope includes setting information on a light source embedded in the wireless endoscope, and wherein the setting information for the wired endoscope includes setting information on a light source that emits illumination light to be supplied to the wired endoscope.

10. The endoscope apparatus according to claim 1,
wherein in a case where the processor switches from the first endoscope in use to the second endoscope not in use and activates the second endoscope not in use and subsequently obtains a detection result indicating switching of the endoscope to be used from the second endoscope to the first endoscope, the processor is configured to read the first setting information for the first endoscope stored in the memory, and use the first setting information for setting the observation function of the first endoscope.

11. The endoscope apparatus according to claim 10,
wherein when the setting for the observation function of the second endoscope is changed during operation of the second endoscope, the processor is configured to update the second setting information for the second endoscope stored in the memory, and based on the updated second setting information for the second endoscope, update the first setting information for the first endoscope, in the memory, and reflect the updated first setting information in the setting information for the second endoscope.

12. A method of controlling an endoscope apparatus, comprising:

detecting a switching signal for switching from a first endoscope in use to a second endoscope not in use, one of the first endoscope and the second endoscope being a wireless endoscope and another of the first endoscope and the second endoscope being a wired endoscope;

after detecting the switching signal, reading second setting information about an operation of the second endoscope stored in a memory, and using the second setting information for setting an observation function of the second endoscope after switching from the first endoscope to the second endoscope; and after setting an observation function of the first endoscope in use is changed, updating a first setting information for the first endoscope in use stored in the memory, and based on the updated first setting information for the first endoscope in use, updating the second setting information for the second endoscope not in use, in the memory, and reflecting the updated second setting information in the setting information for the second endoscope not in use.

13. The method according to claim 12, further comprising:

connecting a first interface to a wireless device, the wireless device wirelessly transmitting and receiving information to and from the wireless endoscope;

connecting a second interface to a connector connected to the wired endoscope; and detecting the switching signal, based on a detection result of at least one of a first detection of detecting connection between the wireless device and the first interface or connection between the connector and the second interface, or a second detection of detecting wireless connection to the wireless device.

14. The method according to claim 13,
wherein the first endoscope is the wireless endoscope, and the second endoscope is the wired endoscope.

15. The method according to claim 12,
wherein the first endoscope is the wireless endoscope, and the second endoscope is the wired endoscope.

16. The method according to claim 12, further comprising:

in a case where the endoscope to be used is switched from the first endoscope to the second endoscope, intermittently driving the wireless device with a predetermined period during use of the second endoscope to determine that the first endoscope becomes usable; and when the first endoscope is determined to be usable during use of the second endoscope, performing switching of the endoscope to be used from the second endoscope to the first endoscope.

17. A non-transitory computer-readable recording medium recording a control program for an endoscope apparatus, the control program causing a computer to at least perform:

detecting a switching signal for switching from a first endoscope in use to a second endoscope not in use, one of the first endoscope and the second endoscope being a wireless endoscope and another of the first endoscope and the second endoscope being a wired endoscope;

when detecting the switching signal, reading second setting information about an operation of the second endoscope stored in a memory, and using the second setting information for setting an observation function of the second endoscope after switching from the first endoscope to the second endoscope; and when setting an observation function of the first endoscope in use is changed, updating a first setting information for the first endoscope in use stored in the memory, and based on the updated first setting information for the first endoscope in use, updating the second setting information for the second endoscope not in use, in the memory, and reflecting the updated second setting information in the setting information for the second endoscope not in use.

18. The non-transitory computer-readable recording medium according to claim 17, wherein the endoscope apparatus comprises:

a first interface to which a wireless device is connectable, the wireless device wirelessly transmitting and receiving information to and from the wireless endoscope; and a second interface connectable to a connector connected to the wired endoscope, and wherein the control program further causes the computer to perform:

detect the switching signal, based on a detection result of at least one of a first detection of detecting connection between the wireless device and the first interface or connection between the connector and the second interface, or a second detection of detecting wireless connection to the wireless device.

19. The non-transitory computer-readable recording medium according to claim 18, wherein the first endoscope is the wireless endoscope, and the second endoscope is the wired endoscope.

20. The non-transitory computer-readable recording medium according to claim 17, wherein the first endoscope is the wireless endoscope, and the second endoscope is the wired endoscope.

* * * * *